United States Patent [19]

Hubbard et al.

[11] Patent Number: 4,872,599
[45] Date of Patent: Oct. 10, 1989

[54] TELEMETRY POUCH WITH EXPANSIBLE CHEST STRAP

[75] Inventors: Vance M. Hubbard, Bedford; Welton K. Brunson, Tarrant County, both of Tex.

[73] Assignee: Tecnol, Inc., Fort Worth, Tex.

[21] Appl. No.: 722,323

[22] Filed: Apr. 12, 1985

Related U.S. Application Data

[63] Continuation-in-part of Ser. No. 576,961, Feb. 3, 1984, which is a continuation of Ser. No. 354,632, Mar. 4, 1982, abandoned.

[51] Int. Cl.$^4$ ................................................ A45F 3/14
[52] U.S. Cl. ..................................... 224/208; 224/901
[58] Field of Search ............... 224/202, 205, 208, 257, 224/258, 219, 901

[56] References Cited

U.S. PATENT DOCUMENTS 4,315,641 2/1982 Larsen ................................. 224/219
4,347,956 9/1982 Berger ................................. 224/202

Primary Examiner—Henry J. Recla
Attorney, Agent, or Firm—Baker, Mills & Glast

[57] ABSTRACT

Provided is a pouch (12) for maintaining hospital telemetry appartus secured to the patient. The pouch (12) includes an open-topped bag (18) formed from opposed flexible side walls (24, 26) joined at the side and bottom edges thereof, the top edges (30, 32) being open to form an opening for the insertion of the telemetry apparatus. A neck and chest strap (22, 20) are each connected to the bag at an extremity thereof, and hooking members (52, 54) are provided to secure the straps at the other extremities thereof to snugly secure the pouch to the patient. Each strap (20, 22) is laminate and includes on one side surface a non-apertured polyester material, and on the other side surface a brushed pile surface engageable with the hooking members (52, 54). The chest strap (20) further includes an elastic section (40) which allows expansion for breathing or stretching of a patient while yet holding the pouch secured to the patient.

1 Claim, 1 Drawing Sheet

U.S. Patent     Oct. 10, 1989     4,872,599
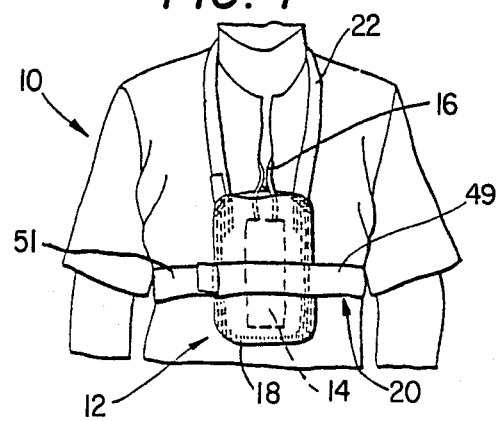
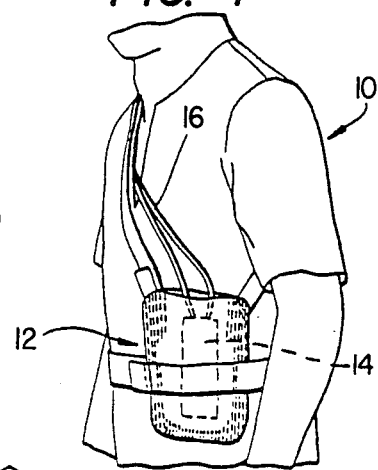
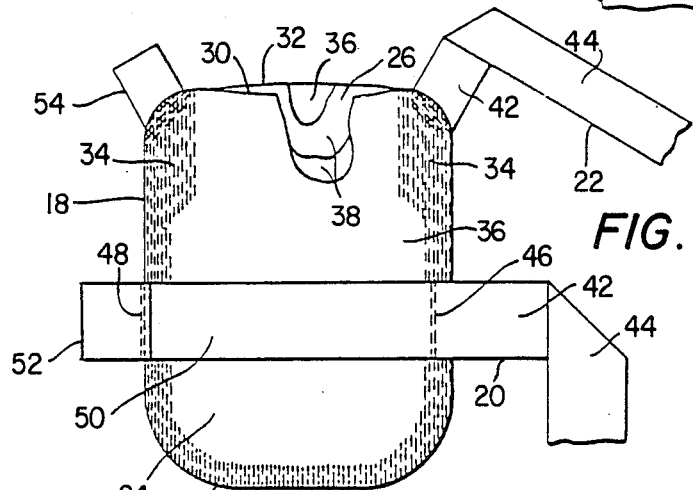
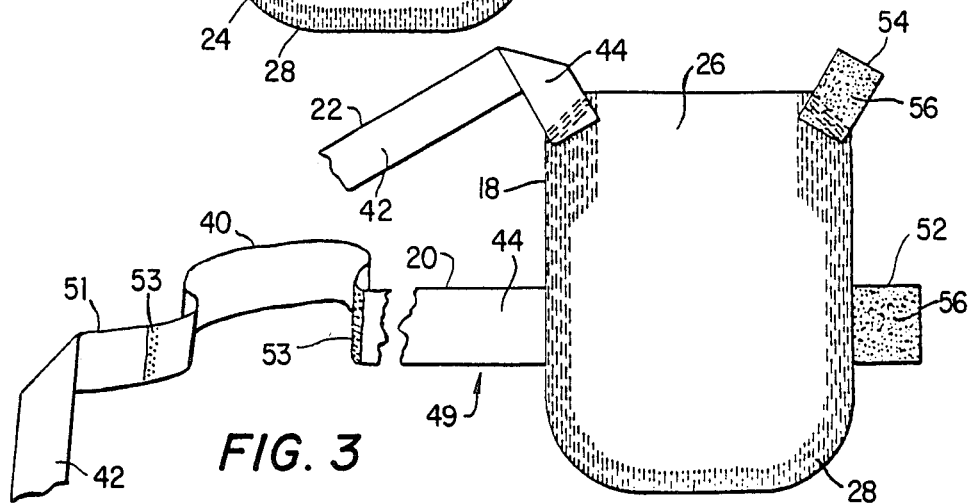

TELEMETRY POUCH WITH EXPANSIBLE CHEST STRAP

RELATED APPLICATIONS

This application is a continuation-in-part of application Ser. No. 576,961, filed Feb. 3, 1984, now abandon which was a continuation of patent application Ser. No. 354,632, filed Mar. 4, 1982, now abandoned.

TECHNICAL FIELD

The present invention relates to medical apparatus, and more particularly to a pouch-like apparatus for removably securing a telemetry unit or the like to a patient.

BACKGROUND OF THE INVENTION

Telemetry monitoring has become widely used in the care of coronary patients. Most major hospitals now have sophisticated equipment to continuously monitor the condition of a coronary patient by portable individual telemetry units and a centralized receiving and recording system.

A major drawback of telemetry monitoring has been the difficulty in positioning, securing and protecting the telemetry unit carried by the patient. The most common methods of attaching the telemetry unit have been to attach the unit to the patient's garment with a safety pin, wrap the unit directly against the patient's skin with an elastic bandage, place the unit inside the pocket of the garment, or use an expensive, reusable holder or pouch. All these makeshift prior art methods are costly, time-consuming, uncomfortable and inconvenient for the patient.

Further, the prior art methods often fail to secure medical telemetry equipment properly to the body of the patient, and excessive movement of the unit creates harmonics which disturb the calibration of the unit, resulting in inaccurate readings. In addition, the straps which have heretofore been used to secure the telemetry pouch to the patient's body are not yieldable and thus do not adjust with body movements. In other words, the straps traditionally used may be cinched tightly to assure securement of the telemetry pouch to the correct location on the patient's body. This is undesirable as the tight straps constrain the breathing and movement of the patient, which is important especially with patients having breathing or cardiac problems. Because there is no prescribed method or widely used device to secure the unit, many are also dropped and damaged. Prior art methods also do not provide moisture-proof protection for the unit. As a result, moisture can impair the accuracy of the readings and damage the telemetry unit, or both.

Thus, it can be seen that a need exists for a telemetry unit holder which will snugly secure the telemetry unit to the body of a patient, yet also be easily adjustable and removable for the comfort and care of the patient, and yieldable for free body movement of the patient.

SUMMARY OF THE INVENTION

The present invention provides a medical pouch adapted to encompass and secure a telemetry unit for telemetry monitoring of hospital patients which substantially eliminates many of the drawbacks of the prior art methods of attachment. Foam and woven material are ultrasonically bonded to form a liquid repellent pouch for the telemetry unit. The foam interlayer helps secure the unit and prevent it from sliding or moving during periods of patient activity. A specially constructed neck strap and an expansible chest strap of ultrasonically bonded pile and woven polyester material in conjunction with a Velcro mushroom fastener provide universal sizing and continuous adjustability.

BRIEF DESCRIPTION OF THE DRAWING

A more complete understanding of the invention and its advantages will be apparent from the Detailed Description taken in conjunction with the accompanying Drawings in which:

FIG. 1 is a view of the telemetry pouch of the present invention attached to a patient in a front position;

FIG. 2 is a partially broken away front view of the telemetry pouch of the present invention;

FIG. 3 is a back view of the telemetry pouch of FIG. 2, illustrating an expansible elastic section of the chest strap; and FIG. 4 is a view of the telemetry pouch of the present invention attached to a patient in a side position.

DETAILED DESCRIPTION OF THE INVENTION

Referring initially to FIG. 1, patient 10 is fitted with pouch 12 in a front position. Telemetry unit 14, shown in phantom lines, is connected to the patient by cables 16. Pouch 12 includes bag 18, first strap 20 and second strap 22. First strap 20 encircles the patient's chest, while second strap 22 loops around the patient's neck. Bag 18 is snugly centered over the patient's chest.

Referring now to FIGS. 2 and 3, bag 18 is constructed of opposed and flexible front wall 24 and back wall 26. Front and back walls 24 and 26 are joined together along periphery 28 thereof, except top edges 30 and 32 of front and back walls 24 and 26 respectively define an upwardly-facing opening in bag 18. Periphery 28 includes wide bonded portions 34 at the extremeties thereof such that the opening defined by top edges 30 and 32 is narrower than the central cavity defined by front and back walls 24 and 26.

In preferred form, front and back walls 24 and 26 are constructed of an outer layer 36 of 1.2 oz. non-apertured polyester material laminated to an inner layer 38 of 0.035 inch polyester foam. Opposing outer layers 36 and inner layers 38 of front and back wall 24 and 26 are laminated to one another by means of ultrasound. Ultrasound bonding is also used to join periphery 28 of front and back walls 24 and 26 to form bag 18.

First and second straps 20 and 22 are similar in construction, except first strap 20 is somewhat wider than second strap 22 in the preferred embodiment, and the first strap 20 includes a section of an elastic material 40. Each strap is an elongate laminate, flexible member having outer surface 42 and inner surface 44. In the preferred form, inner layer is a 1.9 oz. non-apertured polyester material similar to the material used in constructing the bag outer layer 36. A significant feature of the present invention is strap outer layer 42, which is a specially manufactured fabric. Outer strap layer 42 is a knitted fabric that has been brushed to raise individual fibers into a pile, without breaking the individual filaments. The resulting pile fabric is composed of a multiplicity of uninterrupted arches of unbroken individual filaments. In preferred form, strap outer layer 42 is constructed of a 40 denier, 13 filament polyester fabric.

First strap 20 is attached to bag 18 by ultrasound at junctions 46 and 48. End portion 50 of strap 20 is intermediate of junctions 46 and 48. Second strap 22 is attached at an extremity thereof by ultrasound to an upper corner of bag 18.

In accordance with an important feature of the invention, the first strap 20 includes an elastic medial section 40 which is bonded at 53 by ultrasound techniques between first strap sections 49 and 51. In practice, the elastic section 40 comprises a polyester lycra type of material. The elastic section 40 is typically about six inches long, with a width of three fourths inch. With these dimensions of the noted elastic material, the first strap 20 has an elasticity which is well suited to hold the telemetry pouch 12 and equipment 14 therein secured to the patient's body, while yet allowing the patient to breath freely or bend the upper body torso. Adjustment of the first strap 20 tension may be accomplished by means described below.

The elastic section 40 is located between sections 49 and 51 of the chest strap 20 so that it is adjacent the patient's back. This aspect allows first strap sections 49 and 51 to engage the patient's body or garment as shown in FIG. 1 and maintain the pouch 18 centered at a desired location, such as in front of the patient, while yet allowing free body movement for breathing or stretching.

Hooking members 52 and 54 are attached to edges of bag 18, and in preferred form are constructed of mushroom-type Velcro hook material. As shown in FIG. 3, hooking members 52 and 54 have hook sides 56 facing in an opposite direction to that of outer layer 42 of straps 20 and 22, such that hook sides 56 and outer layers 42 oppose one another when straps 20 and 22 are wrapped around patient 10. In the preferred embodiment, where outer layer 42 faces outwardly, hook sides 56 of hooking members 52 and 54 face inwardly. The unbroken and raised fiber filaments of outer layer 42 form loops which mesh with hook sides 56 of hooking members 52 and 54. The outer layer 42 is responsive to pressure against the hooking members 52 and 54 for removably attaching the two together.

In operation, first strap 20 is wrapped around the waist or chest of patient 10 until the elastic section 40 is stretched to the desired tension, and then snugly secured by meshing hooking member 52 to outer layer 42 of strap 20. The entire outer layer 42 of strap 20, except for the elastic section 40, is constructed of the pile fabric, and therefore, the circumference of strap 20 is infinitely adjustable for comfort and for all sizes of patients. Strap 22 is likewise infinitely adjustable, and may be looped underneath an arm of patient 10 in the side position shown in FIG. 4 or around the neck of patient 10 in the front position of FIG. 1. The non-woven outer layer 36 of bag 18 is moisture-proof, thereby eliminating perspiration or liquid damage to telemetry unit 14 during use.

The use of specially constructed pile material for outer layer 42 enables the inexpensive construction of pouch 12. The provision of standard Velcro-type pile material in sufficient lengths for infinite adjustability of straps 20 and 22 would not be cost-effective, because standard Velcro pile fabric is very expensive and inappropriate for use in a disposable product such as pouch 12.

Foam inner layer 38 is a high-friction surface which serves to both cushion and prevent shifting of telemetry unit 14. The high friction of inner layer 38 in combination with wide bonded portions 34 of periphery 28 prevents telemetry unit 14 from slipping out when patient 10 is in a bending or prone position.

Pouch 12 secures and protects telemetry unit 14 during monitoring, and has numerous advantages over makeshift or costly reusable-type holders. The design of pouch 12 and the fabric combinations used in the construction of pouch 12 ensures increased accuracy of telemetry readings.

What is claimed is:

1. A pouch for maintaining hospital telemetry apparatus adjacent a patient while being sufficiently low cost in construction and materials as to be economically disposable after use, comprising:

an open-topped bag formed from opposed sidewalls fabricated from 1.2 ounce non-apertured polyester material joined at the side and bottom edges thereof by heat sealing with ultrasound such that a flexible moisture proof exterior is formed that is dimensioned to receive the telemetry apparatus and allow the telemetry apparatus to protrude therefrom and which prevents perspiration or liquid damage to the apparatus during use;

an inner layer disposed adjacent the innermost side of at least one of the said opposed sidewalls and ultrasonically bonded thereto, and fabricated from 0.035 inch polyester foam material to provide a high friction causing layer, said inner layer preventing substantial movement of the telemetry apparatus within said bag such that forces on the telemetry apparatus directed outward from the opening in said bag do not result in separation of said bag and the telemetry apparatus, the flexibility of said bag enhancing the friction applied by said inner layer;

said opposing sides joined together in such a manner that the interior of said bag opens outwardly from the open top thereof to the bottom thereof in such a manner that objects within the pouch are restricted from removal;

a first strap having first and second ends and being dimensioned to fit around the body of the patient, said first strap being heat sealed with ultrasound at said first end to one of said side edges of said bag, said first strap having an inner side and an outer side, substantially the entire inner side is fabricated from non-apertured polyester material and said outer side manufactured from a knitted fabric having the surface thereof brushed to raise individual fibers into a pile thereby forming a multiplicity of uninterrupted arches of unbroken individual filaments, and a section of elastic material spliced by heat sealing with ultrasound into said first strap;

hooking material attached to the side edge of said bag opposite said first end of said strap for hooking with said outer side first strap such that said bag is secured to the body of said patient when said first strap is disposed about the body of said patient and attached to the hooking member;

a second strap having first and second ends dimensioned to fit around an upper portion of the body of the patient, said second strap being heat sealed with ultrasound at said first end to an upper corner of said bag, said second strap having an inner side and outer side, said inner side fabricated from non-apertured polyester material and the entire said outer side fabricated from knitted fabric having the surface thereof brushed to raise individual fibers into a pile composed of a multiplicity of uninterrupted arches of unbroken individual filaments;

a hooking layer attached to the upper corner of said bag opposite said first end of said second strap for mating with the outer side of said second strap such that said bag is maintained at a desired height relative to the body of the patient; and said first and second straps adjustably securing said bag to body of said patient and said foam inner layer in said bag preventing dislodging of the telemetry apparatus contained therein for all directions of motion of said patient, whereby said pouch is completely constructed with ultrasound techniques to increase the speed and reduce the cost of manufacture thereof.

* * * * *